United States Patent [19]

Urdea et al.

[11] Patent Number: 5,256,549
[45] Date of Patent: Oct. 26, 1993

[54] PURIFICATION OF SYNTHETIC OLIGOMERS

[75] Inventors: Michael S. Urdea, Alamo; Thomas Horn, Berkeley, both of Calif.

[73] Assignee: Chiron Corporation, Emeryville, Calif.

[21] Appl. No.: 517,526

[22] Filed: Apr. 27, 1990

Related U.S. Application Data

[63] Continuation of Ser. No. 229,475, Aug. 3, 1988, abandoned, which is a continuation-in-part of Ser. No. 891,789, Jul. 30, 1986, abandoned, which is a continuation-in-part of Ser. No. 845,290, Mar. 28, 1986, abandoned.

[51] Int. Cl.$^5$ .............. C12P 19/34; C07K 1/04; C07K 1/06; C07K 1/14
[52] U.S. Cl. ................. 435/91; 935/88; 530/334; 530/335; 530/336; 530/337; 530/344; 536/25.3; 536/25.31; 435/91.5; 435/91.3
[58] Field of Search .............. 435/90, 91, 196, 219, 435/287; 530/333, 334, 335; 935/88

[56] References Cited

U.S. PATENT DOCUMENTS

| | | | |
|---|---|---|---|
| 4,483,964 | 11/1984 | Urdea et al. | 435/287 |
| 4,517,338 | 5/1985 | Urdea et al. | 435/287 |
| 4,521,509 | 1/1985 | Benkovic et al. | 435/91 |

OTHER PUBLICATIONS

Phillippsen et al., "Splitting of Phenylalanine Specific tRNA into Half-Molecules by Chemical Means", Biochem Biophys Res. Comm. vol. 33, 922–928, 1968.
McBride et al., "Amidine Protecting Groups for Oligonucleotide Synthesis" J. Am. Chem. Soc., vol. 108, 2040–2048, 1986.

*Primary Examiner*—George C. Elliott
*Attorney, Agent, or Firm*—Dianne E. Reed; Kenneth M. Goldman; Robert P. Blackburn

[57] ABSTRACT

Oligomers and polymers are prepared substantially free of error sequences by sequentially adding monomers, which are terminally blocked and have active functionalities protected, to a growing chain bound to a support through a selectively cleavable linkage. After each addition, unblocked terminal groups are capped. At the completion of monomer addition, enzymatic hydrolysis interfering protecting groups are removed along with the capping group and failure sequences enzymatically degraded. The terminal blocking group may then be removed. The completed oligomer or polymer may be cleaved from the support prior or subsequent to enzymatic degradation but after completion of the sequence.

29 Claims, 1 Drawing Sheet

PURIFICATION OF SYNTHETIC OLIGOMERS

CROSS-REFERENCE TO RELATED APPLICATIONS

This application is a continuation of application Ser. No. 07/229,475, filed Aug. 3, 1988 and now abandoned, which is a continuation-in-part of application Ser. No. 06/891,789, filed Jul. 30, 1986 and now abandoned, which is a continuation-in-part of application Ser. No. 06/845,290, filed Mar. 28, 1986 and now abandoned.

BACKGROUND OF THE INVENTION

1. Field of the Invention

With the advent of hybrid DNA technology and the explosion in the ability to isolate, purify, and assay a wide variety of natural products, both polypeptides and nucleic acids, there is an increasing need for rapid and efficient methods for preparing oligomers of amino acids and nucleic acids.

With nucleic acids, there is the need to synthesize sequences for use as linkers, adapters, synthetic genes and synthetic regulatory sequences, as well as probes, primers, and the like. While only small amounts of materials are required in the initial application, since these sequences can be cloned, it is very important that the sequences be substantially free of sequences which include errors, since such sequences could result in constructions which result in undesired products or results.

For the poly(amino acids) or polypeptides, there is substantial interest in being able to synthesize naturally occurring polypeptides for investigation of their physiological properties, for production of polypeptide fragments and natural products, where such fragments can be studied for their physiological properties, be used as haptens for the production of antibodies specific for a determinant site of interest, drug agonist or antagonist, or the like.

Many procedures have been developed for producing oligomers of nucleotides, amino acids or other naturally occurring monomers. These procedures for the most part rely on attaching the first monomer by a selectively cleavable linkage to a solid support. Each monomeric unit is then added sequentially, with each addition involving a number of chemical reactions.

At each stage during the synthesis of the oligomer, there is a small but finite probability that a number of chains will not be extended. Therefore, during the oligomerization, a large number of errors may be introduced, where sequences are produced having single or multiple omissions of monomers. At the completion of the sequence and separation from a support, the desired sequence will be contaminated with sequences closely approximating the desired sequence. These errors may then manifest themselves in a number of different ways, varying with whether a polynucleotide or polypeptide is being prepared. With polynucleotides, when the sequences are being cloned and used in various constructions, errors may have been introduced where the clone which is selected includes the erroneous sequence. Without prior oligomer purification during sequencing of the construct, the error may be retained leading to undesired products, suboptimum performance, or the like. With polypeptides, the erroneous sequence may lead to different physiological activity from the intended sequence, the formation of antibodies binding to sequences other than the sequence of interest and possibly providing for erroneous results, as a result of the varying binding response.

It has therefore become of increasing importance to be able to prepare sequences with an assurance that there is substantially no contamination of sequences approximating the desired sequence, which would lead to erroneous products or observation. By removing failure sequences during preparation, one may also avoid the need for subsequent purifications, such as electrophoresis, which can result in loss of material. Loss of material can be a serious problem when dealing with the very small amounts of materials synthesized in initial stages involving cloning or investigative polypeptides.

2. Description of the Prior Art

Matteucci and Caruthers, *J. Am. Chem. Soc.* (1981) 103:3185–3191, describe the use of phosphorchloridites in the preparation of oligonucleotides. Beaucage and Caruthers, *Tetra. Lett.* (1981) 22:1859–1862 and U.S. Pat. No. 4,415,732 describe the use of phosphoramidites in the preparation of oligonucleotides. Smith, *ABL* Dec. 1983) 15–24, describes automated solid phase oligodeoxyribonucleotide systhesis. See also the references cited therein. See also, Warner et al., *DNA* (1984) 3:401–411, whose disclosure is incorporated herein by reference.

Amidine protection of adenosine has been described by McBride and Caruthers, *Tetra. Lett.* (1983) 24:245 and Froehler and Matteucci, *Nucl. Acids Res.* (1983) 11:8031. Other blocking groups will be described in the description.

SUMMARY OF THE INVENTION

Novel methods and compositions are provided involving production of condensation oligomers, where individual monomers are members of a predetermined group and are added sequentially to provide a predetermined sequence of the individual monomers. The oligomerization occurs while the growing chain remains bound to an insoluble support. After each stage, failure sequences are capped and the next monomer added until the sequence is complete. Protective groups on the individual monomers, terminal blocking groups, capping groups, and linkage to the support are selected so as to allow for selectable cleavage. The blocking groups are selected so as not to interfere with enzymatic degradation of a sequence lacking the terminal blocking group or may be selectively removed at the time of removal of the capping group. At completion, the capping group is removed, blocking groups which interfere with enzymatic degradation are removed, and incomplete sequences lacking the terminal blocking group are degraded enzymatically. The oligomers may be retained on the support or removed prior to enzymatic degradation of the incomplete sequences. The completed correct sequences are then isolated substantially free of sequences having errors.

DESCRIPTION OF THE SPECIFIC EMBODIMENTS

The subject invention concerns oligomerization of monomers having common functional groups but differing in side chains. The monomers undergo condensation type oligomerization, where the chain is extended while being bound to a support. The oligomerization involves stepwise addition of monomers to produce a desired sequence of at least about 10 members, usually at least about 12 members, and the number of members may be 100 or more. Various functional groups are employed for a variety of functions, which can be selectively removed. The functional groups include side chain protective groups, terminal blocking groups, capping groups, and linking groups, for maintaining the oligomer bound to the support. These functionalities are chosen, so that they may be selectively removed or cleaved during the preparation of the oligomer and/or after completion of the sequence, while retaining the sequence bound to the support, during the oligomerization and optionally during enzymatic degradation of incomplete sequences.

In addition, protective groups are employed which either do not interfere with exohydrolase degradation of error or incomplete sequences, or may be selectively removed prior to the enzymatic hydrolysis. Cleavage of the completed sequence from the support before or after degradation of the error or incomplete sequences is reflected and after separation from the support and degradation of the incomplete sequences, the completed sequences may then be isolated substantially free of the materials associated with the preparation of the sequence.

The subject method provides for selective removal of error containing or incomplete oligomers. This is achieved by employing terminal blocking functionalities which inhibit an exohydrolase from acting on a complete sequence, while the exohydrolase is capable of hydrolyzing an unblocked incomplete sequence. The method also requires employing capping functionalities which terminate sequences which have not undergone the next stage in the sequential addition, and prior to capping, retain the reactive free terminal functionality. Thus, failure sequences terminate at the time of failure and are not continued.

While any condensation oligomerization may be employed, which allows for the selective employment of blocking and linking groups, for the most part, the subject invention will be directed to nucleic acids, i.e., DNA and RNA, and poly(amino acids), although the same strategy could be effective in the preparation of polysaccharides, both carbohydrate and aminosaccharides. Each polymer or oligomer will employ the same functionality for linking between the individual condensation monomers; for nucleic acids, phosphate esters will be employed; for amino acids, peptide or amide bonds; for sugars, hemiacetal or -ketal ether bonds will be employed.

The following formula is a generalized depiction of the monomers employed in the subject invention:

wherein:

M intends the central residue of the molecule, which includes all that portion of the molecule which is not involved in the formation of the oligomeric linkages, nor in blocking or protecting, e.g., in the case of glycine it would be methylene, in the case of adenosine it would include all of the molecule excent the group bonded to phosphorus and the blocked oxy-group involved in the formation of the phosphate ester link;

$\alpha$ is the functionality, either in activable or active form for reacting with the terminal functionality of the oligomer;

$\beta$ is the terminal functionality, which when unblocked reacts with $\alpha$;

$\gamma$ is the blocking group of $\beta$;

$\delta$ is a functionality which requires protection, usually amino, hydroxy or mercapto, and which may or may not be present;

$\epsilon$ is the protective group;

$\mu$ is the blocking group of $\mu$; and a will be equal to the number of functionalities which must be protected, generally ranging from 0 to 2, more usually from 0 to 1.

When the composition is a purine, the purine nucleotides employed in the subject invention will for the most part have the following formula:

wherein:

$M^1$ is an adenine or guanine residue with the exocyclic amino group at the 2 or 6 position for guanine and adenine, respectively;

Z is an O-blocking group;

one of $B^1$ or $G^1$ may be hydrogen and the other a protective group, or the two may be taken together to define a protective group doubly bonded to nitrogen;

W is a pair of electrons or oxygen, being a pair of electrons when Y is a disubstituted amino group and oxygen when Y is oxy;

Y is oxy or a disubstituted amino group, where the substituents are organic groups which do not interfere with the course of the reaction and the disubstituted amino group serves as a leaving group for the formation of a phosphate ester;

oxy is usually an ammonium salt, conveniently a trialkylammonium salt of from 3 to 12 carbon atoms;

when Y is a disubstituted amino group it will be of the formula $-NT^1T^2$, where $T^1$ and $T^2$ are the same or different and are organic groups;

D is an organic group which is selectively removable; and

E is hydrogen or a protective group.

When the nucleotides are pyrimidines the pyrimidines will have the following formula:

wherein all of the symbols have been defined previously except for:

$M^2$ is a cytosine or thymine residue;

when $M^2$ is a cytosine residue, b is 1, while when $M^2$ is a thymine residue, b is 0;

$B^2$ is hydrogen and $G^2$ is a protective group, usually acyl.

Groups employed for D will be aliphatic groups, particularly saturated aliphatic groups, β-heterosubstituted aliphatic groups, where the β-substituent is an electron withdrawing group which readily participates in β-elimination, either as the leaving group or the proton activating group, α-substituted methylene, where the α-substituent may vary widely and supports a negative charge on the methylene through inductive or resonating effects; aryl; and aralkyl. Depending on the nature of the phosphorus functionality, one group may be chosen over another. Thus, depending upon whether a phosphorchloridite, phosphoramidite, phosphate, thiophosphate, phosphite, or the like, is employed, particular phosphoro ester groups will be preferred.

For phosphorchloridites and phosphoramidites, alkyl and β-substituted dimethylenes will be preferred, while for phosphates and phosphines, aryl and aralkyl functionalities will be preferred.

For the most part, D may be illustrated by the following formula:

$$Q(CH_2)_c-C^1(J_2)-$$

wherein:

1 intends the first carbon atom;

the J's are the same or different, being H or alkyl of from 1 to 3, usually 1 to 2 carbon atoms, preferably methyl;

c is 0 or 1, usually being 0 or 1 when Q is bonded through a carbon atom and 1 when Q is bonded through a heteroatom;

Q may be H, alkyl of from 1 to 9 carbon atoms, nitrato, methylsulfonyl, cyano, phenyl, benzyl, phenyl-, benzyl-, substituted phenyl-, substituted benzylthio or -sulfoxy, where the number of aryl substituents will be 0 to 2 and are illustrated by cyano, halo, nitro, etc., trihalomethyl, particularly fluoro and chloro, β-naphthyl, 9-fluorenyl, 2-anthraquinonyl, etc. or D may be phenyl or substituted phenyl, where the substituents may be the same as indicated above and in addition may include trityl bonded directly to phenyl or through oxygen or carbon.

Specific groups reported for use as D are as follows:

| | |
|---|---|
| alkyl | Beaucage and Caruthers, Tetrahedron Lett. (1981) 22:1859 |
| NCCH$_2$C(Me)$_{0-2}$(H$_{2-0}$)— | Koster, Nucleic Acids Res. (1984) 12:4539; Marugg et al., Rec. trav. Chim. Pay-Bays (1984) 103:97-8; Van Boom et al., Nucleic Acids Res. (1984) 12:8639 |
| p-O$_2$NφCH$_2$CH$_2$— | Schwarz and Pfleiderer Tetrahedron Lett. (1984) 25:5513 |
| MeSo$_2$CH$_2$CH$_2$— | Claesen et al., ibid (1984) 25:1307 |
| (halo)$_3$CC(Me)$_{0-2}$(H)$_{0-2}$— | Takaku et al., Chemistry Letters 1984:1267; Letsinger et al., Tetrahedron (1984) 40:137 |
| φ(CH$_2$)$_{0-1}$S(O)$_{0-2}$(CH$_2$)$_2$ | Balgobin et al., Tetrahedron Lett. (1981) 22:1915; Agarwal et al., J. Am. Chem. Soc. (1976) 98:1065; Felder et al., Tetrahedron Lett. (1984) 25:3967 |
| (χ)$_{0-2}$φCH$_2$—, 2-naphthyl-CH$_2$—, 9-fluorenyl-CH$_2$—, 2-anthraquinonyl-CH$_2$— | Caruthers et al., Nucleic Acids Res. Sym. Ser. (1980) 7:215; Christodonlon & Reese, Tetrahedron Lett. (1983) 24:1951; Kwiatkowski et al., Abstract, Conf. on Syn. Oligonucleotides in Molecular Biology, Uppsala, Sweden Conf. 16–20 (1982) #64; Balgobin, ibid |
| (χ)φCH$_2$CH$_2$— | Uhlmann et al., Tetrahedron Lett. (1980) 21:1181; Schulz and Pfleiderer, ibid (1983) 24:3582; Beite and Pfleiderer, ibid (1984) 25:1975 |
| MeCOCH(Me)— | Ramirez et al., Tetrahedron (1983) 39:2157 |
| φ$_3$Cφ(Cl)— | Vasseur et al., Tetrahedron Lett. (1983) 24:2573 |

χ may be hydrogen or any non-interfering stable substituent, neutral or polar, electron donating or withdrawing, generally being of 1 to 10, usually 1 to 6 atoms and generally of from 0 to 7 carbon atoms, and may be an aliphatic, alicyclic, aromatic or heterocyclic group, generally aliphatically saturated, halohydrocarbon, e.g., trifluoromethyl, halo, thioether, oxyether, ester, amide, nitro, cyano, sulfone, amino, azo, etc. For each of the various $χ^x$, where x is a numeral, they will come within the definition of χ, but those skilled in the art will be able to select the appropriate groups in light of the subject disclosure. In some instances, preferred χ groups will be indicated or $χ^x$ may be redefined.

The groups which are employed as D will be removable by reagents which do not remove the terminal blocking group or, as appropriate, cleave the oligomer from the support, such as phenyl- or substituted phenylmercaptides and tert.-amines, ammonia, aldoximates, organic amine solvents including mono- or polyamines.

The groups which are employed for Z will be aralkyl groups, particularly substituted and unsubstituted pixyl or triarylmethyl, where the aryl groups may be phenyl, naphthyl, furanyl, biphenyl, etc., and the substituents will be from 0 to 3, usually 0 to 2 and come within the definition of χ.

The groups employed as Z will be stable to the reagents employed for removal of protective groups and capping groups, being primarily stable to base and sensitive to acid. Thus benzyl, particularly α-substituted such as trityl groups, find use as the terminal blocking group.

In some situations it may be desirable to substitute for Z with a different group after completion of the synthesis of the oligomer. Depending upon the blocking group, particularly where a trityl group is employed, and the nature of the enzyme employed to degrade the incomplete oligomers, the hydrolytic conditions may result in a significant proportion of the Z groups being removed. Under these conditions, complete oligomers may also be degraded resulting in substantial diminution of the yield of the oligomer.

In order to avoid degradation of complete oligomers by an exonuclease, the Z group may be replaced with a different blocking group, which is stable under the conditions of the exonucleolytic conditions. Such a group will be characterized by being retained during the removal of the capping group, being retained during the exonucleolytic conditions, and being removable without degradation of the oligomer, either by itself or in conjunction with cleavage from the support.

Rather than remove the blocking group and substitute an alternative group, depending upon the substitute blocking group, e.g., carboxylic acid ester, phosphate, etc., the ultimate nucleotide may be prepared with the substitute blocking group present. Thus, by having preprepared nucleotides containing the substituted blocking group, these may be added in the last step where the manual or automated procedure permits using a different nucleotide.

For the most part, the groups substituted for Z'will be acyl groups which provide for stable esters. The acyl groups may be organic or inorganic. Acyl groups, including carboxyl, phosphoryl, pyrophosphoryl, and the like. Of particular interest are alkanoic acids, more particularly aryl substituted alkanoic acids, where the acid will be of at least 4 carbon atoms and not more than about 12 carbon atoms, usually not more than about 10 carbon atoms, with the aryl, usually phenyl, substituted alkanoic acids usually of from 8 to 12 carbon atoms. Various heteroatoms may be present such as oxygen (oxy), halogen, nitrogen, e.g., cyano, etc. For the most part, the carboxylic acid esters will be base labile, while mild acid stable, particularly at moderate temperatures below about 50° C., more particularly, below about 35° C. and at pHs greater than about 2, particularly greater than about 4.

In some situations, specialized reagents may be employed, which provide for the desired protection. For example, an O-dibromomethylbenzoate may be employed to provide the ester, which may then be cleaved with specific reagents as will be described below.

The following Table indicates a number of groups which may be employed and references describing the groups used as blocking groups and conditions and reagents for removing the groups.

| Substitute Blocking Groups ($Z^s$) | Reference |
| --- | --- |
| trityloxyacetyl | Werstiuk and Neilson, Can. J. Chem. (1972) 50:1283 |
| benzoate | Stawinski et al., J. C. S. Chem. Comm. 1976:243 |
| phenoxyacetyl | Jones and Reese, J. Am. Chem. Soc. (1979) 101:7399; Reese, Tetrahedron (1978) 23:3143 |
| aryl substituents 4-Cl, 2,6-di(Cl)-4-Me | |
| dihydrocinammyl | Sachdev and Starkovsky, Tetra. Lett. 1969:733 |
| pivaloate | van Boeckel and van Boom, Tetra. Lett. 1979:3561; Griffith et al., Tetrahedron (1968) 24:639 |
| phosphoryl | van der Marel et al., Tetra. Lett. 1981:1463; J. G. Nadeau, et al., Biochem. (1984) 23:6153; F. Himmelsbach and W. Pfleiderer, Tetra. Lett. (1982) 23:4793; J. E. Marugg, et al., Nucl. Acids Res. (1984) 12:8639; A. Kondo, et al., Nucl. Acids Res. Symp. Ser. (1985) 16:161 |
| pyrophosphoryl | |
| O-dibromomethylbenzoyl* | Chattapadhyaya et al., J. Chem. Soc. Chem. Comm. 1979:987 |
| phenylisocyanate | Agarwal and Khorana, J. Am. Chem. Soc. (1972) 94:3578–3585 |

*Removal involves treatment with AgClO$_4$, followed by the removal of silver as halide and addition of morpholine.

The benzoate groups may be readily removed with the enzyme α-chymotrypsin. Phosphate may be removed with alkaline phosphatase. Other enzymes which may be employed include carboxypeptidase A, leucine aminopeptidase, acid phosphatase, pyrophosphatase, etc. Alternatively, instead of using enzymatic hydrolysis, the carboxylate ester groups may be removed by ammonium hydroxide, sodium hydroxide, morpholine, etc.

Of particular interest are specific phosphorylating agents, which can be used for phosphorylating an hydroxyl group of a nucleoside, for example, the terminal 5'-hydroxyl of the completed sequence. Of particular advantage in the subject invention is the use of the novel O,O'-di(cyanoethyl) phosphoramidite, where the nitrogen may be substituted (1–2 groups) or unsubstituted, particularly disubstituted, more particularly, dialkyl substituted, with alkyl groups of from 1 to 6, usually 2 to 4 carbon atoms, particularly 3 carbon atoms, e.g. isopropyl. (See the description of $-NT^1T^2$ below.)

The subject agent can be used as the substitute blocking group ($Z^s$), providing for a phosphite ester, which may be oxidized and the O-substituents removed in the same manner as nucleosidyl phosphoramidites used as monomers. The subject reagent permits easy functionalization of the terminal hydroxyl of the oligomer, provides protection of the completed chain, and is readily compatible with automated synthesis of nucleic acid sequences.

The groups employed for Y will depend upon the nature of the phosphorus derivative employed for oligomerization. When the phosphoramidite is employed, Y will have the formula $-NT^1T^2$, where $T^1$ and $T^2$ may be the same or different and may be hydrocarbon or have from 0 to 5, usually 0 to 4 heteroatoms, primarily oxygen as oxy, sulfur as thio, or nitrogen as amino, particularly tert.-amino, NO$_2$, or cyano. The two T's may be taken together to form a mono- or polyheterocyclic ring having a total of from 1 to 3, usually 1 to 2 heteroannular members and from 1 to 3 rings. Usually, the two T's will have a total of from 2 to 20, more usually 2 to 16 carbon atoms, where the T's may be aliphatic (including alicyclic), particularly saturated aliphatic, monovalent, or, when taken together, divalent radicals, defining substituted or unsubstituted heterocyclic rings. The amines include a wide variety of saturated secondary amines such as dimethylamine, diethylamine, diisopropylamine, dibutylamine, methylpropylamine, methylhexylamine, methylcyclopropylamine, ethylcyclohexylamine, methylbenzylamine, methylcyclohyxylmethylamine, butylcyclohyexylamine, morpholine, thiomorpholine, pyrrolidine, piperidine, 2,6-dimethylpiperidine, piperazine and similar saturated monocyclic nitrogen heterocycles. (U.S. Pat. No. 4,415,732)

Specific groups reported for use as $-NT^1T^2$ are as follows:

| | |
| --- | --- |
| N-pyrrolidino | Beaucage, Tetrahedron Lett. (1984) 25:375, Schwarz and Pfleiderer, ibid (1984) 25:5513 |
| N = $\chi^1$ $\chi^1$ - alkylene of 4–12 carbon atoms, p-bis-dimethylenecyclohexane, bis-diethylene sulfide and methylamino | |
| N $\chi^1$; $T^1$, $T^2$-Me, iPr | McBride and Caruthers, ibid (1983) 24:245 |
| $\chi^1$ - bis-diethyleneoxy, α,α,α',α'-tetramethylpentamethylene nitroimidazole, tetrazole | Matteucci and Caruthers, J. Am. Chem. Soc. (1981) 103:3185 |

Illustrative groups include: N-pyrrolidino, N-piperidino, 1-methyl-N-piperazino, N-hexahydroazipino, N-octahydroazonino, N-azacyclotridecano, N-3-azabicyclo-(3.2.2.)nonano, thiomorpholino, N,N-diethylamino, N,N-dimethylamino, N,N-diisopropylamino, piperidino, 2,2,6,6-tetramethyl-N-piperidino.

Y may also be halo, e.g., chloro (Letsinger and Lunsford, *J. Am. Chem. Soc.* (1976) 98:3655; Matteucci and Caruthers, supra.) or an ammonium oxy salt, particularly trialkylammonium of from 3 to 12 carbon atoms.

When preparing RNA or mixed RNA-DNA oligomers, particularly using the triester method, groups employed as E are as follows:

| | |
|---|---|
| $\chi\phi CH_2$ | Takaku et al., J. Org. Chem. (1984) 49:51; Ohtsuka et al., Tetrahedron Lett. (1981) 22:765 |
| 2-tetrahydropyranyl | Ohtsuka et al., ibid (1984) 40:47 |

Other groups which may be used include trisubstituted silyl, e.g., trialkylsilyl of from 3 to 12 carbon atoms, 2-tetrahydrofuranyl, tert-butyldimethylsilyl or other protective group stable to basic conditions and the condensation conditions.

The exocyclic amine protective groups will be selected to be stable to the condensation conditions and removable at completion of the sequence without removal of the terminal blocking group or, as appropriate, cleavage of the linking group to the support or, alternatively, not interfere with the degradation of the error sequences. B and G may be the same or different and may be taken together to define a divalent radical. When not taken together, usually B will be hydrogen.

When B is hydrogen, G will usually be acyl of from 2 to 16, usually 2 to 14 carbon atoms and from 0 to 6 (excluding the oxo oxygen), usually 0 to 4 heteroatoms which are chalcogen (oxygen and sulfur) or nitrogen, where nitrogen is usually bonded to other than hydrogen and may be aliphatic, alicyclic, aromatic, heterocyclic, or combinations thereof and may be substituted or unsubstituted, usually free of aliphatic unsaturation, where substituents include alkyl or alkoxy of from 1 to 6 carbon atoms, halo, nitro, phenyl, dialkylamino of from 2 to 6 carbon atoms, oxo, etc., and includes derivatives of formic and carbonic acid.

For the most part when B is H, G will be of the formula:

$$(\chi^2)_c\text{---}\Delta\text{---}CO$$

wherein:

$\Delta$ is an aliphatic or alicyclic radical of 1 to 10, usually 1 to 6 carbon atoms, usually saturated, or an aryl (including heterocyclic of from 1 to 2 heteroatoms which are chalcogen or nitrogen) where the rings are of from 5 to 6 annular members, of from 1 to 2 rings and of from 5 to 12 carbon atoms, or an aralkyl, where the aryl is as defined above and alkyl is of from 1 to 3 carbon atoms;

c is 0 when $\Delta$ is aliphatic and 0 to 3, usually 0 to 2 when $\Delta$ is aryl or aralkyl;

$\chi^2$ is alkyl or alkoxy of from 1 to 6, usually 1 to 4 carbon atoms, halo, particularly chloro, phenylazo, nitro, cyano, etc.

When B and G are taken together to form a divalent radical, the divalent radical will be alkylidene or dioyl of from 3 to 12 carbon atoms and 0 to 4 heteroatoms other than the oxo atoms of the dioyl, and may be aliphatic, alicyclic, aromatic or heterocyclic, or combinations thereof, the alkylidene forming an imine or amidine, the dioyl forming a cyclic imide, where the alkylidene will usually be alkylidene of from 1 to 3 carbon atoms, α-substituted with a disubstituted amino, particularly dialkylamino group of from 2 to 10 carbon atoms, while the dioyl will be of from 4 to 12 carbon atoms.

Specific groups reported for use as B and G are as follows:

| | |
|---|---|
| alkyl-CO<br>alkyl-Me, iPr, t-butyl,<br>MeCOCH$_2$CH$_2$—, t-butyl$\phi$OCH$_2$ | Schaller et al., J. Am. Chem. Soc. (1963) 85:3821; Koster et al., Tetrahedron (1981) 37:363; Olivivie et al., Tetrahedron Lett. (1982) 38:2615 |
| $\chi^3$-aryl-CO<br>aryl-$\phi$, pyridyl,<br>$\chi^3$-MeO, $\phi$N$_2$, Me, Cl, NO$_2$<br>t-butyl | Koster et al., supra |
| $\chi^3$-aryl(CH$_2$)$_{0-2}$OCO | Himmelsback and Pfleiderer, Tetrahedron Lett. (1983) 24:3583; Watkins and Rappaport, J. Org. Chem. (1982) 47:4771; Watkins et al., J. Am. Chem. Soc. (1982) 104:5702 |
| <br>—CH≡<br>Me$_2$NCH≡, (n-Bu)$_2$NCH≡,<br>N—Me-pyrrolidinylidene-2, | Holy and Zwemlicka, Collection Czechoslovakian Chemical Comm. (1969) 34:2449; McBride and Caruthers, Tetrahedron Lett. (1983) 24:2953; Froehler and Matteucci, Nucleic Acids Res. (1983) 11:8031 |
| —CO-π-CO—<br>π-ethylene, o-phenylene, chloro substituted o-phenylene | Kume et al., ibid (1984) 12:8525 |

Among the above components are certain preferred groups. For the terminal blocking group, the triarylmethyl groups, particularly dimethyoxytrityl are preferred for the monomers during synthesis. For the exocyclic amino protective group, alkylidene, particularly dibutylaminomethylene is preferred.

The next functionality of importance is the linkage of the oligomer to the support. The linkage should be stable during the various stages of the oligomerization, the removal of capping and protective groups, and usually the blocking groups, and, as appropriate, the hydrolytic degradation of the error sequences. The choice of the linkage unit including the functionality for releasing the completed oligomer will be affected by the support, the monomer and nature of blocking groups and phosphorus group, the capping group and the reagents employed for the oligomerization.

A wide variety of supports have found employment, such as silica, Porasil C, polystyrene, controlled pore glass (CPG), kieselguhr, poly(dimethylacrylamide), poly(acrylmorpholide), polystyrene grafted onto poly(tetrafluoroethylene), cellulose, Sephadex LH-20, Fractosil 500, etc. References of interest include: Matteucci and Caruthers, supra, Chow et al., *Nucleic Acids Res.* (1981) 9:2807; Felder et al., *Tetrahedron Lett.* (1984) 25:3967; Gough et al., ibid (1981) 22:4177; Gait et al, *Nucleic Acids Res.* (1982) 10:6243; Belagaje and Brush, ibid (1982) 10:6295; Gait and Sheppard, ibid (1977) 4:4391; Miyoshi and Itakura, *Tetrahedron Lett.* (1978) 38:3635; Potapov et al., *Nucleic Acids Res.* (1979) 6:2041; Schwyzer et al., *Helv. Chim. Acta* (1984) 57:1316; Chollet et al., ibid (1984) 67:1356; Ito et al., *Nucleic Acids*

Res. (1982) 10:1755; Efimov et al., ibid (1983) 11:8369; Crea and Horn, ibid (1980) 8:2331; Horn et al., *Nucleic Acids Res. Sym. Ser.* (1980) 7:225; Tragein et al., *Tetrahedron Lett.* (1983) 24:1691; Koster et al., *Tetrahedron* (1984) 40:103; Gough et al., *Tetrahedron Lett.* (1983) 24:5321; Koster et al., ibid (1972) 16:1527; Koster and Heyns, ibid (1972) 16:1531; Dembek et al., *J. Am. Chem. Soc.* (1981) 103:706; Caruthers et al., *Genetic Engineering: Principles and Methods*, eds. Setlow and Hollaender, Vol. 4, 1982, pp. 1-12, Plenum Press, N.Y.

Depending on the nature of the support different functionalities will serve as anchors. For silicon containing supports, such as silica and glass, substituted alkyl or aryl silyl compounds will be employed to form a siloxane or siloximine linkage. With organic polymers, ethers, esters, amines, amides, sulfides, sulfones, phosphates may find use. For aryl groups, such as polystyrene, halomethylation can be used for functionalization, where the halo group may then be substituted by oxy, thio (which may be oxidized to sulfone), amino, phospho (as phosphine, phosphite or phosphate), silyl or the like. With a diatomaceous earth, e.g., kieselguhr, the diatomaceous earth may be activated by a polyacrylic acid derivative and the active functionality reacted with amino groups to form amine bonds. Polysaccharides may be functionalized with inorganic esters, e.g., phosphate, where the other oxygen serves to link the chain. With polyacrylic acid derivatives, the carboxyl or side chain functionality, e.g., N-hydroxethyl acrylamide, may be used in conventional ways for joining the linking group.

The linking group or chain will vary widely as to length, functionalities and manner of linking the first nucleotide. For extending chains, functionalities may include silyl groups, ether groups, amino groups, amide functionalities or the like, where bifunctional reagents are employed, such as diamines and dibasic acids, amino acids, saccharides, silanes, etc.

A number of supports and linking groups which have been reported in the literature are shown in the following Table.

TABLE

| Support[1] | Linking chain[2] | Terminal group[3] | Reference |
|---|---|---|---|
| Silica | $Si(CH_2)_3NHCO(CH_2)_2CO-$ | DMT-nucleoside | Mateucci & Caruthers, 1980, supra |
| Silica | Si— (5' att) | 3'Ac-Thymidine | Koster, Tetrahedron Lett. (1972) 16:1527 |
| Silica | $(Si\phi C(\phi_2)O-$ (5' att) | Ac-nucleoside | Koster, Tetrahedron Lett. (1972) 16:1527 |
| CPG | $LCAA-CO(CH_2)CO-$ | $2'$-o-$O_2N\phi CH_2$, 5'DMT-ribonucleoside | Gough et al., ibid (1981) 22:4177 |
| CPG | $SiOSi(OEt)_2(CH_2)_3NHCO(CH_2)_2CO-$ | DMT-nucleoside | Koster et al., Tetrahedron (1984) 40:103 |
| CPG | $LCAA-CO(CH_2)_2CO-$ (5' att) | $2'$-$\phi CO$-ribonucleoside | Gough et al., Tetrahedron Lett. (1983) 24:5321 |
| Porasil C | $Si(CH_2)_3NHCO(CH_2)_2CO-$ | DMT-nucleoside | Chow et al., Nucleic Acids Res. (1981) 9:2807 |
| Kieselguhr - PDMA | $N(Me)CH_2CONH(CH_2)_2-$ $(COCH_2NH)_2CO(CH_2)_2CO$ | DMT-nucleoside | Gait et al., ibid (1982) 10:6243 |
| Polystyrene | $CH_2SO_2(CH_2)_2OP(Cl\phi O))_2-$ | DMT-nucleoside | Felder et al., Tetrahedron Lett. (1984) 25:3967 |
| Polystyrene | $CH_2O\phi C(\phi)(MeO\phi)O-$ (5' att) | nucleoside-(3'-Cl$\phi$-phosphate) | Belagaje & Brush, Nucleic Acids Res. (1982) 10:6295 |
| Sephadex LH-20 | $OPO_2-$ (5' att) | ribonucleoside | Koster & Heyns, Tetrahedron Lett. (1972) 16:1531 |
| Polyacrylamide | $CONH(CH_2)_2NHCO(CH_2)_2CO-$ | CMT-nucleoside | Dembek et al., J. Am. Chem. Soc. (1981) 103:706 |
| Fractosil 500 | $(CH_2)_3NH(CH_2)_2CO-$ | CMT-nucleoside | Caruthers et al., Genetic Engineering (1982) 4:12 |
| Polyacryl morpholide | $(CH_2)_nNH-$ | ribo- or deoxyribonucleoside | S. Pochet et al., Tetrahedron Lett. (1985) 26:627 |
| Silica | " | ribo- or deoxyribonucleoside | S. Pochet et al., supra |
| CPG(LCAA) | " | ribo- or deoxyribonucleoside | S. Pochet et al., supra |

[1] CPG - controlled pore glass/PDMA - polydimethylacrylamide
[2] $\phi$ - phenyl/Me - methyl/Et - ethyl/LCAA - long chain alkyl amino/att - attachment
[3] DMT - p,p'-dimethoxytrityl/Ac - acetyl/$\phi$ - phenyl nucleoside intends deoxyribonucleoside/groups indicate O-protective groups/3' nucleoside attachment, unless otherwise indicated Various techniques are described in the literature for producing polynucleotides. For example, phosphoramidite in situ preparation, Beaucage, *Tetrahedron Lett.* (1984) 25:375; the phosphate triester paper disk method, Frank et al., *Nucleic Acids Res.* (1983) 11:4365 and Mathes et al., *EMBO* (1984) 800; the phosphate triester-1-hydroxybenzotriazole method, van der Marel et al., *Nucleic Acids Res.* (1982) 7:2337; ibid (1984) 12:8639; the phosphate triester-arylsulfonyltetrazole coupling method, Stawinski et al., ibid (1977) 5:353; the phosphate triester barium salt method, Gough et al., ibid (1979) 7:1955, the phosphate triester filtration method, Chaudhuri et al., *Tetrahedron Lett.* (1984) 25:4037; reverse phosphitylation, Jayaraman and McClaugherty, *Biotechniques*, 1984, 94; reverse direction phosphate triester (5' to 3') method, Belagaje and Brush, *Nucleic Acids Res.* (1982) 10:6295, phosphoramidite method, Beaucage and Caruthers, *Tetrahedron Lett.* (1981) 22:1859; phosphochloridite method, Matteucci and Caruthers, *J. Am. Chem. Soc.* (1981) 103:3185; phosphite "syringe" method, Tanaka and Letsinger, *Nucleic Acids Res.* (1982) 10:3249; methyl phosphoroditetrazolide (MPDT)-phosphite method, Cao et al., *Tetrahedron Lett.* (1983) 24:1019; cyanoethyl phosphoramidites, Sinha et al., *Nucleic Acids Res.* (1984) 12:4539; and nitrophenethyl phosphoramidites, Beitzer and Pfleiderer, *Tetrahedron Lett.* (1984) 25:1975.

The remaining reagent is the capping agent, which serves to cap the failure sequences having free hydroxyl groups. For the most part, the capping group will be a carboxylic acyl group, particularly of from 2 to 8, more usually of from 2 to 6 carbon atoms and having from 0 to 2 heterosubstituents, which include oxygen, sulfur and nitrogen, particularly oxygen as oxy or oxo, sulfur as thioether or sulfone, and nitrogen as amino nitrogen free of hydrogen atoms covalently bonded thereto. Illustrative capping groups include acetyl, levulinyl, arylthiourethanyl, particularly phenyl, and dimethoxytriazolylphosphine. The capping reagents and the manner of their use is described in references cited previously, Matteucci and Caruthers, and Chow et al., as well as Agarwal and Khorana, *J. Am. Chem. Soc.* (1972) 94:3578, which references are incorporated herein by reference.

Various combinations will be preferred. For example, in preparing nucleic acids in the 3'-5' direction the preferred terminal blocking group will usually be a trityl group, where the aryl groups may be varied, as well as the substituents, with the dimethoxytrityl being preferred. As the exocyclic amine protective group, preferred groups will include the methylene group, particularly dialkylaminomethylene, alkanoyl, particularly branched alkanoyl, and aroyl, particularly benzoyl and substituted benzoyl. As the linking functionality, carboxylic acid esters, glycols, and trityl ethers will find use. As the capping functionality, of particular interest are the carboxylic acid capping groups, particularly acetyl and levulinyl.

Various combinations of protective, blocking, capping and linking functionalities may be employed in conjunction with various reagents for removing or cleaving the associated functionalities. The following combinations are illustrative.

| FUNCTIONALITY[1] | REAGENT | CONDITIONS |
|---|---|---|
| [1]P—O CH$_3$ | φSH | φSH/TEA/Dioxane (1:1:2 v/v) 1 h |
| —N =CHNBu$_2$ (A,G) | hydrazine | 0.5M N$_2$H$_4$.H$_2$O in pyridine-acetic acid (4:1 v/v), 18 h/20° |
| —COC$_6$H$_5$ (C) | | |
| B dimethoxytrityl | aq. acid | 80% aq. acetic acid, 1 h/20° |
| L succinate | base | conc. aq. NH$_4$OH, 2 hr/20° |
| C levulinyl | hydrazine | conc. aq. NH$_4$OH, 15 min/20° |
| [2]P—O Cl-φ | oximate | 1M tetramethylguanidiniumpyridinealdoximate |
| CH$_3$ | φSH | 1M tetramethylguanidiniumpyridinealdoximate |
| N iso-butyryl (G) benzoyl (A,C) | aq. NH$_4$OH | conc. aq. NH$_4$OH, 60°/5 h |
| B dimethoxytrityl | aq. acid | 80% aq. acetic acid, 1 h |
| C acetyl | aq. NH$_4$OH | conc. aq. NH$_4$OH, 20°/1 h |
| L 3'-3'phosphotriester | 1) photolysis 2) Pb$^{2+}$ | 1) λ = 350 nm in ethanol 2) 0.1M aq. lead (II) acetate, pH 7-8, 18 h/37° |

KEY TO PRECEDING PAGE:
[1]P—O protective group for oxygen on phosphorus
N protective group for exocyclic amines
B 5'-blocking group
C 5'-capping group
L linkage to support
R = o-NO$_2$-φ-CH$_2$—

As illustrated above, for removal of the protective group for an exocyclic amino group, aqueous ammonia and hydrazine may be employed, which will also serve to remove the capping group.

Upon removal of enzymatic hydrolysis interfering protective functionalities or all blocking groups except for the terminal 5' or 3' moiety on the desired product, enzymatic hydrolysis of truncated failure sequences is conducted. Enzymes for the hydrolysis will be chosen on the basis of rate, 5' to 3' or 3' to 5' hydrolysis (depending on the direction of synthesis), inhibition by a terminal blocking group, lack of endonuclease activity and a lack of sequence or secondary structural dependence. For 3' to 5' synthetic routes spleen phosphodiesterase (Bernardi and Bernardi, 1971, The Enzymes, Ed. P. D. Boyer, 3rd edition, V.4, p. 271, Academic Press, N.Y.), *Bacillus subtilis* extracellular exonuclease (Kerr et al. *J. Biol. Chem.* (1967) 242:2700, Kanamore et al., *Biochim. Biophys. Acta*, (1974) 335:173; Kanamore et al., *Biochim. Biophys. Acta*, (1974) 335:155), salmon testes exonuclease (Menon and Smith, *Biochem.* (1970) 9:1584), and *Lactobacillus acidophilus* phosphodiesterase (Fires and Khorana, *J. Biol. Chem.*, (1983) 238:2798) may be used. For 5' to 3' synthetic routes, snake venom phosphodiesterases (Laskowski, 1971, In The Enzymes, Ed. P. D. Boyer, 3rd edition, V.4, p. 313, Academic Press, N.Y.), mouse kidney phosphodiesterase (Razzell, W. E., *J. Biol. Chem.*, (1961) 236:3031), carrot exonuclease (Harvey et al., *Biochemistry*, (1967) 6:3689; Harvey et al., *Biochemistry* (1970) 9:921) and avena leak phosphodiesterase (Udvardy, *Biochim, Biophys. Acta*, (1970) 206:392) may be used. Appropriate conditions for the assays may be found in the references cited.

Polypeptides may also be used in the subject invention, sharing many analogies to the nucleic acids. For the polypeptides, the terminal blocking group will usually be the group bonded to the α-amino group, although the synthesis may be in the reverse direction with carboxyl as the terminal group. The protective groups will be those groups bonded to side chain amino, hydroxyl, mercapto, and carboxy groups, as found in lysine, arginine, histidine, tyrosine, serine, threonine, cysteine, aspartic acid and glutamic acid. In addition, various resins are employed, where the completed chain must be cleaved from the resin and it is desirable to cap those chains where addition has failed to occur, much the same as the nucleic acid chains.

For the most part, the amino acids employed for building the chains will have one of the following formulas, depending upon whether the chain is built in the C-N direction or in the N-C direction, that is whether the terminal functional group on the chain is carboxy or amino.

wherein:

J and J¹ are residues of amino acids, either the D- or L-amino acid and include any of the normal side chains of the 20 natural amino acids, or unnatural amino acids, such as homoserine, norleucine, sarcosine, etc.;

K and K¹ are functional protective groups, differing in their nature depending upon whether the functionality is amino (which may further be distinguished by whether the amino is an amino group, guanidine or imidazole) hydroxy, mercapto, or carboxy; for amino, the protective groups may include, α, β-unsaturated ketones of from 4 to 12 carbon atoms, oxycarbonyls of from 2 to 12, usually from 4 to 10 carbon atoms, particularly aliphatic, aromatic, and aralkyl being acid labile, β-diketones, arylsulfenyl, arylsulfonyl, aralkyl, nitro, and polynitrophenyl;

for hydroxyl, aralkyl of from 7 to 12 carbon atoms and aryloxycarbonyl, both substituted and unsubstituted;

for mercapto, alkyl and aralkyl of from 1 to 10 carbon atoms which may contain sulfur to form a disulfide, e.g., methyl thio to form methyl dithio;

for carboxy, aralkyl of from 7 to 12 carbon atoms, both substituted and unsubstituted or alkyl from 2 to 7 carbon atoms;

for the terminal blocking group Q, for an amino terminal group, oxycarbonyl of from 2 to 12, more usually from 5 to 10 carbon atoms, which are aliphatic, alicyclic, aromatic, or combinations thereof; diacyl, capable of forming a cyclic imide of from 5 to 6 annular members; aralkyl, particularly trityl, both substituted and unsubstituted, and polyfluorocarboxylic acids of from 2 to 4 carbon atoms, particularly perfluoro, while Q¹ will be hydrogen, where the terminal group is carboxy;

where the terminal group is amino, U may be hydroxy or an ester group capable of forming an amide bond to an amino acid in an aqueous medium and will include such groups as N-oxy succinimide, o-nitrophenyl, pentachlorophenyl, 4-oxy-3-nitrobenzene sulfonic acid, or a mixed anhydride, particularly with a carbonic acid derivative;

U¹, which will serve as the terminal group may be alkyl or aralkyl of from 1 to 10 carbon atoms.

The remaining valence on the nitrogen will be hydrogen if not otherwise substituted.

As a generalized reference to various blocking groups and protective groups, see Barany and Merrifield, *Peptides: Analysis, Synthesis, Biology*, Vol. 2, Special Methods, (eds. Gross and Meienhofer), 1979.

The following is an illustrative list of protective groups found in the literature:

| Amino acid protective groups | |
|---|---|
| NH₂ | |
| enamine | U.S. Pat. Nos. 3,645,966 |
| oxycarbonyl | 3,645,996; 3,915,949; |
| alkyl thio carbonyl | Anfinsen, Pure and App. Chem. (1968) 17:461 Kollonitsch et al., Chem. Ber. (1956) 83:2288-2293 |
| methylsulfonylethyloxycarbonyl | Tesser and Balvert-Geers, Int. J. Pept. Protein Res. (1975) 7:295 |
| dialkylphosphinothioyl | van den Akker and Jellinek, Recl. Trav. Chim. Pays-Bas. (1967) 86:897 |
| dithiasuccinoyl | Barany and Merifield, J. Am. Chem. Soc. (1977) 99:7363 |
| β-diketo | U.S. Pat. No. 3,645,996 |
| o-NO₂φS | U.S. Pat. No. 3,915,949 |
| tosyl | U.S. Pat. No. 4,062,815 |
| trifluoroacetic | Anfinsen, supra; Atherton et al., (1979) "Peptides" (Siemion and Kupryszewski, eds.) p. 207-210, Wroclaw Univ. Press, Wroclaw, Poland; Jones, Tet. Lett. 1977:2853; Schlatter et al., Tet. Lett. 1977:2851 |
| benzyl (im) | Anfinsen, supra; Atherton et al., (1979) "Peptides" (Siemion and Kupryszewski, eds.) p. 207-210, Wroclaw Univ. Press, Wroclaw, Poland; Jones, Tet. Lett. 1977:2853; Schlatter et al., Tet. Lett. 1977:2851 |
| NO₂ (guanidine) | Anfinsen, supra; Atherton et al., (1979) "Peptides" (Siemion and Kupryszewski, eds.) p. 207-210, Wroclaw Univ. Press, Wroclaw, Poland; Jones, Tet. Lett. 1977:2853; Schlatter et al., Tet. Lett. 1977:2851 |
| fluorenylmethoxycarbonyl | Chang et al., (Int. J. Peptide and Protein Res. (1980) 15:485 |
| 2,4-dinitrophenyl | U.S. Pat. No. 4,487,715 |
| trityl | Zervas and Theodoropoulos, J. Am. Chem. Soc. (1956) 78:1359-1369 |
| OH | |
| benzyl | U.S. Pat. No. 3,914,949 |
| BrφOCO | U.S. Pat. No. 4,062,815 |
| SH | |
| benzyl | U.S. Pat. No. 3,743,628 |
| alkyl 1-4 carbon atoms | U.S. Pat. No. 4,062,815 |
| S-alkylmercapto | Friedman (1973) "The Chemistry and Biochemistry of the Sulfhydryl Group in Amiono Acids, Peptides and Proteins," Pergamon, Oxford |
| CO₂H | |
| benzyl | U.S. Pat. No. 3,915,949; Anfinsen, supra |
| 2-oxymethyleneanthraquinone | Kemp and Reczek, Tet. Lett. (1977) 12:1031 |

In addition to the particular blocking groups and protective groups, there is also the functionality involved with the linkage to the support and the nature of the support. A wide variety of supports have found use in conjunction with polypeptide synthesis. Supports include such diverse materials as cross-linked polystyrene, cellulose, polyvinyl alcohol, glass, polyethyleneimine, and the like. Employing such supports, a wide variety of linkages have been employed for linking the initial amino acid to this support. Linkers include esters, amides, and substituted amines, depending upon whether the polypeptide terminus is amino or carboxyl.

Illustrative of supports found in the literature and linking functionalities are the following:

| Supports and linking functionalities | |
|---|---|
| x-linked polystyrene, HOCH₂-cellulose polyvinyl alcohol, HOCH₂-sulfonated polystyrene; substituted polystyrene | U.S. Pat. Nos. 3,743,628; 3,645,996 |
| p-oxybenzyl resin glass beads | U.S. Pat. No. 3,814,732 |
| vinylbenzene amino acid esters | U.S. Pat. No. 4,060,689 |
| p-methylene-nitrobenzamide linker | U.S. Pat. No. 4,062,815 |
| polyethyleneimine | Blecher and Pfaender, Liebigs Ann. Chem. 1973:1263 |
| thiophenylethoxy linker | Gait and Sheppard, Nucleic Acids Res. (1977) 4:4391; Schwyzer et al., Helv. chim. acta (1984) 57:1316 |
| o-NO₂CH₂O—, o-NO₂φNCO linkers | Rich and Gurwara, JCS Chem. Comm. (1973) 1973:610; J. Amer. Chem. (1975) 97:6, 1575; Zehavi et al., J. Org. Chem. (1972) 37:2281; J. Am. Chem. Soc. (1973) 95: 5673 Fridkin et al., J. Am. Chem. Soc. (1965) 87:4646; Merrifield, J. Am. Chem. Soc. (1963) 85:2149 Schlatter et al., Tet. Lett. 1977:2851; Jones, Tet. Lett. 1977:2853 Atherton et al., (1979) "Peptides" (Siemion and Kupryszewski, eds.), p. 207-210, Wroclaw Univ. Press, Wroclaw, Poland |
| anchoring through a trypsinolysable group | Meyers and Glass, Proc. Natl. Acad. Sci. USA (1975) 72:2193; |

| Supports and linking functionalities | |
|---|---|
| | Gross et al., Angew. Chem. Int. Ed. (1973) 12:664; (1975) in "Peptides, 1974" (Y. Wolman, ed.) p. 403-413, Wiley, N.Y. |

As capping groups, one may use the same type of group employed as the side chain protective group for amines, but differing from the terminal blocking group. In this manner, capping groups and side chain protective groups may be removed simultaneously prior to enzymatic degradation of error sequences.

Illustrative capping groups for amino termini include trityl, polyfluoroacyl, fluorenylmethoxycarbonyl, dithiasuccinoyl, o-nitrophenylsulfenyl and 2,4-dinitrophenyl.

Upon completion of the oligomeric polypeptides, the various functionalities involved with the protective, capping and blocking groups may be cleaved and the groups removed, followed by cleavage from the support. The following table illustrates various combinations of functionalities and reagents.

| | FUNCTIONALITY[1] | | REAGENT | CONDITIONS |
|---|---|---|---|---|
| 1 | C → N | | | |
| | P—O | | | |
| | S | S-alkylmercapto | φSH | aq. φSH pH 7.5-9 0.1M in pyridine, 30 min |
| | N | dithiasuccinoyl (Lys) | φSH | aq. φSH pH 7.5-9 0.1M in pyridine, 30 min |
| | | dinitrophenyl (His, Tyr) | φSH | 0.1H φSH in DMF, 30 min |
| | COO | phenacyl (Asp, Glu) | φSH | 1M NaSφ in DMF, 8 h/25° |
| | B | BOC | TFA | 20-50% TFA in CH₂Cl₂, 30 min/20° |
| | C | dinitrophenyl | φSH | Same as above |
| | L | o-nitrobenzyl ester | photolysis | λ = 350 nm in ethanol, 24 h/20° |
| | | oxymethyleneanthaquinone | reduction | Na dithionite in dioxane-H₂O, 8 h |
| 2 | C → N | | | |
| | P—O | | | |
| | S | S-alkymercapto | φSH | same as under 1 |
| | N | dithiasuccinoyl (Lys) | φSH | " |
| | | dinitrophenyl (His, Tyr) | φSH | " |
| | COO | phenacyl (Asp, Glu) | φSH | " |
| | B | Fmoc | piperidine | 50% in CH₂Cl₂, 30 min/20° C. |
| | C | dinotrophenyl | φSH | same as under 1 |
| | L | o-nitrobenzyl ester | photolysis | same as under 1 |
| 3 | N → C | | | |
| | P—O | | | |
| | S | S-alkylmercapto | φSH | same as under 1 |
| | N | dithiasuccinoyl (Lys) | φSH | " |
| | COO | phenacyl (Asp, Glu) | φSH | " |
| | B | tert-butyl ester | TFA | 50% TFA-CH₂Cl₂, 30 min |
| | C | methyl ester | TFA | same as above |
| | L | o-nitrobenzylamine | photolysis | 320 nm, 1 hr |

P—O protecting group on side chain oxygen
S protecting group on side chain sulfur
N protecting group on side chain nitrogen
COO protecting group on side chain carboxylate
B terminal blocking group
C capping group
L linkage to support As indicated above in example 1, in preparing the polypeptides, when the terminal amino acid has been added, by having employed thiolysable groups as protective groups and capping groups, the protective and capping groups may be preferentially removed in the presence of oxycarbonyl terminal blocking groups. Thus, using conditions such as thiophenol under basic conditions protective and capping groups may be removed, while retaining α-amino terminal blocking groups. The error sequences may then be degraded employing amino peptidases, such as amino peptidase M (Royer and Andrew, *J. Biol. Chem.* (1973) 248:1807–1812). After degradation, the terminal protecting group and the linkage to the support may be cleaved simultaneously or sequentially, depending upon the particular groups. For example, with oxo-carbonyls and a group allowing for β-elimination, e.g., sulfonylethyl, the amino acid chain could be released from the support and deblocked simultaneously.

Where the carboxyl group is the terminus, terminal blocking groups may include tertiary alkyl or aralkyl groups, which are acid labile, while employing base-labile side chain protection groups, such as polyfluoroacetyl groups or thiolysable side chain protecting groups (see above). The error sequences could then be degraded with carboxy peptidases A, B or C or combinations thereof. An illustrative sequence could be as follows. An ester would be formed with the first amino acid to an o-nitrobenzyl linking functionality, which is photolabile. The terminal blocking group could be tert.-butyl oxycarbonyl (tBOC). Thiolysable side chain protecting groups would be employed, such as S-alkylmercapto, dithiasuccinoyl, dinitrophenyl, phenacyl, or the like. Thus, the side chain protection groups could be removed, while retaining the terminal blocking group.

Where the carboxy is the terminal group, different reagents may be employed as blocking, protective and capping groups. For example, the amino group may be anchored to the support by an acid and base-stable linkage, which linkage may be cleaved by hydrogenolysis, e.g., sulfenyl, or photolytic cleavage. The terminal blocking group could be the acid labile tert.-alkyl group which can be removed with trifluoroacetic acid in methylene dichloride. Alternatively, tBOC hydrazinyl could be employed as the terminal blocking group, which could be removed with a reagent such as 4N HCl/dioxane. The side chain protective groups would be base labile groups, such as fluorenylmethyloxy carbonyl (Fmoc) and thiolysable groups (see above), while capping could be a lower alkyl group, such as methyl. After degrading the error sequences, the terminal blocking group may be removed, followed by cleavage from the support and isolation and optionally purification of the completed polypeptide.

Although normally not necessary, various techniques may be employed for further purification to remove other materials which may be present, such as dialysis, gel permeation chromatography, HPLC, reverse phase HPLC, affinity chromatography, or the like.

The supports which are used will vary depending upon whether a manual or automatic process is employed for the preparation of the various sequences. Generally, for an automated procedure, the particle size will be in the range from about 50–300 microns, more usually from about 100–200 microns, while the size of the particles may be at the lower range of the scale, generally from about 100–150 microns where manual synthesis is employed.

To illustrate polynucleotide synthesis, the following exemplification is provided.

Conveniently, an ester linkage to the first nucleoside may be formed by activating the carboxylic acid of the linking group to the support with an appropriate carbodiimide or activated carbonyl, e.g., carbonyl diimidazole, by reaction with a carboxylic acid anhydride or mixed anhydride or other conventional technique.

Once the nucleosidyl ester conjugated support has been prepared, it may now be used for initiating the extension of the polynucleotide chain. Since each of the series of steps is repetitive, for each sequence involving the addition of a nucleotide, the first step will be the removal of the blocking group from the terminal nucleotide bound to the support. As already indicated, for the most part, the blocking group will be a trityl group. Conventionally, this group is removed by a Lewis acid, either a metal halide, e.g., zinc bromide, or a proton acid, particularly a strong carboxylic acid ($pK_a < 4$) such as dichloroacetic acid, trichloroacetic acid, etc., in an inert organic medium, e.g., dichloromethane. The concentration of the Lewis acid will generally be about 0.1 to 1.0M. The time for the reaction will generally vary from about 1 to 5 min, the time being selected to ensure that the reaction is complete, while minimizing any side reactions. This step is common to either procedure involving phosphoramidites or phosphate triesters.

The particles are then washed with an appropriate inert solvent or solvent mixture or series of solvents, particularly organic polar solvents, ending with a wash with an inert anhydrous polar organic solvent to ensure the absence of any moisture, e.g., acetonitrile, dichloromethane, etc. As appropriate, the steps are carried out in the presence of an inert anhydrous environment, such as argon, hydrogen, helium, nitrogen, or the like. Usually, the final wash at each stage will be the solvent system for the next stage.

After a thorough washing to remove any traces of acid, the conjugated particles are now ready for the addition of the next nucleotide. Depending upon the particular phosphorus acid derivative which is employed, the protocols will now vary. Where the phosphoramidite is employed, the phosphoramidite is added in conjunction with an activating agent, such as tetrazole. The conditions for the reaction are the use of an inert anhydrous polar solvent, e.g., acetonitrile for a short time period, generally under 5 min, usually about 1 to 3 min sufficing. In the triester route, the addition of the trialkylammonium salt of the phosphate is carried out in the presence of an activating agent, such as mesitylenesulfonyl-3-nitro-1,2,3-triazole or mesitylenesulfonyl chloride and N-methyl imidazole, that is, an activated aryl sulfonic acid compound.

The condensation with the phosphorous compound is followed by a thorough wash with an inert anhydrous polar organic solvent, e.g., acetonitrile.

With the phosphoramidite, the next stage may be varied, where capping will alternate with oxidation. That is, the phosphite must be oxidized to the phosphate ester.

For capping, a carboxylic acid derivative will be employed which allows for efficient removal of the capping group in conjunction with the amine protecting group. The preferred carboxylic acids will be aliphatic carboxylic acids particularly oxo-substituted of from 2 to 8, usually 2 to 5, carbon atoms which may have a carbonyl group spaced to allow a reaction with hydrazine to form a cyclic compound, usually from 5 to 6 annular members. Of particular interest is acetic or levulinic acid, conveniently as their anhydrides, which may be used to form the ester.

The capping reaction will be carried out by first adding a basic solution containing a heterocyclic aromatic amine or a mixture of amines, particularly a dialkylaminopyridine, more particularly 4-dimethylaminopyridine (DMAP), at about 0.1 to 1M, usually 0.4 to 0.6M, in a solution of about 5 to 20, usually about 10 volume percent of a dialkylated pyridine in a polar ether of from 4 to 6 carbon atoms, e.g., tetrahydrofuran. After adding the above amine solution, the aliphatic carboxylic acid anhydride at about 1 to 3M, preferably 2M, in a polar ether solvent is added. Thus, the heterocyclic aromatic base serves to activate the hydroxyl groups for reaction with the carboxylic acid derivative to produce the ester, capping failed sequences.

For oxidation, the oxidation is carried out conventionally, conveniently employing a mild oxidizing agent, such as iodine in a basic solution, generally from about 0.1 to 0.4, preferably about 0.2M iodine, in a polar aliphatic ether, containing a small amount of a dialkylpyridine, e.g., 2,6-lutidine, and water, the amine base and water, each being from about 5 to 15 volume percent. Alternatively, organic hydroperoxides may be employed, such as t.-butylhydroperoxide or benzylhydroperoxide.

Between the capping step and the oxidation step, a wash is employed, which will use the solvent system of the next step. Since water is employed in the oxidation and an anhydrous system is preferred for the capping, in this sequence, capping will normally be performed first. For the triester sequence, no oxidation is necessary, so capping follows immediately upon condensation.

After washing thoroughly, preferably with successive solvents which are inert anhydrous organic solvents, such as acetonitrile and dichloromethane, the procedure is ready to be repeated. Once the polynucleotide chain has been extended to its desired length, the removal of the protecting groups, degradation of failure sequences, and isolation of the desired sequence may now begin.

The next step is conventional in removing the substituent on oxygen, which is alkyl or substituted alkyl. Conventionally, thiophenoxide is employed in the presence of a trisubstituted amine. Conveniently, an inert ethereal organic solvent is used, such as dioxane. Times will vary widely, depending upon the nature of the system. The time may be as few as about 5 min and as much as about 1 hr. Conveniently, ratios of solvent, mercaptide and amine will be 2:1:1 by volume. The removal of the aliphatic phosphate ester group will be followed by washing with a polar organic hydroxylic compound, particularly alkanolic, e.g., methanol. Where the substituent on oxygen is chlorophenyl, an anhydrous basic solution of an oximate, typically 2-pyridinyl aldoximate, and 1,1,3,3-tetramethyl guanidine may be employed under conventional conditions.

In the next stage, the capping group, e.g., levulinic acid, and amino protecting groups are simultaneously removed. The reagent is hydrazine in a highly polar basic organic solvent, containing a small amount of an organic ammonium salt, such as the salt of an aliphatic carboxylic acid of from 2 to 4 carbon atoms, e.g., acetic acid, with a heterocyclic amine, which amine also serves as the solvent. Desirably, the solvent will be a heterocyclic aromatic base, such as pyridine or substituted pyridine of from 5 to 8 carbon atoms, where the amount of carboxylic acid will generally be from about 10 to 30, preferably from about 15 to 25 volume percent. The hydrazine, as the hydrate, will generally be from about 0.2 to 1M, preferably about 0.5M. The reaction time will be at least 1 hr, more usually at least 6 hr, and not more than about 48 hr, preferably not more than about 24 hr, with temperatures varying from about ambient to 50° C. The reaction is followed by a polar organic hydroxylic solvent wash, particularly methanol, and then dried. The method of drying is not critical, conveniently, a high vacuum at room temperature will suffice.

At this point, failed sequences will have a free hydroxyl group, while successful sequences will terminate in the trityl blocking group. Where the trityl group is to be substituted with a different group, the trityl group may be removed using mild acid as described below. Usually, detritylation and reblocking will occur prior to removal of the capping and protective groups. Thus, the nucleoside protecting functionalities will be present inhibiting reaction at those sites. The terminal hydroxyl may then be reblocked employing an acyl anhydride, e.g. benzoic anhydride, with a tertiary amine, e.g. a combination of N,N-dimethylaminopyridine (DMAP) and 2,6-lutidine in tetrahydrofuran, where the 2,6-lutidine will be about 1:10 (V/V), the anhydride about 0.2 to 2M and the DMAP, about 3 to 10% (W/V). The time will usually vary from about 5 to 30 min at ambient conditions.

The failed sequences are now degraded employing enzymatic degradation, particularly a phosphodiesterase. The medium employed will optimize the activity of the enzyme, usually employing a buffered aqueous medium. The enzyme may be added in a buffered medium 1:1 water:polyol, particularly glycerol. The reaction may be carried out at an elevated temperature, not exceeding about 40° C., generally from about 25° to 40° C., preferably from about 35° to 40° C., and will usually require an extended period of time, usually not less than about 1 hr and not more than about 24 hr. At the completion of the reaction, the medium may be cooled and the support is then washed with an aqueous buffered medium having a pH of about 6 to 7, preferably about 6.4 to 6.5. The concentration of the buffer will generally be from about 0.05 to 0.2M.

The polynucleotide sequence may now be removed from the support, if not previously removed, and the terminal hydroxyl group deblocked. Removal from the support is readily achieved employing a reactive amine, e.g., ammonia, more particularly concentrated aqueous ammonium hydroxide. Where removal occurs prior to deblocking, removal may be accomplished in conjunction with removal of protective groups, employing the severer conditions of removal to simultaneously remove the protective groups. The reaction proceeds relatively rapidly at ambient temperatures, normally being carried out for from about 0.5 to 6 hr, preferably from about 1 to 3 hr. At the completion of the reaction, the particles are removed from the polynucleotide sequence, conveniently by centrifugation, followed by isolation of the nucleotide sequence, conveniently by evaporation of the solvent medium.

An alternate means by which the enzymatic hydrolysis of truncated failure fragments may be conducted in the presence of the 5'-protected target fragment is to remove the failure and target from the support prior to addition of the enzyme. This requires that the 5'-protecting group be stable during the removal of the DNA from the support. With ammonium hydroxide sensitive linkages, 5'-dimethoxytrityl, monomethoxytrityl, trityl, phosphoryl, pyrophosphoryl and other groups can be used. Alternate linkages would permit other 5'-protecting groups.

Enzymatic degradation can be conducted either with the enzyme in solution followed by removal of the activity (e.g. phenol extraction) or with a solid-supported enzyme (e.g. spleen phosphodiesterase; Seliget et al., *Biotechnology and Bioengineering*, Vol. XXII, John Wiley and Sons, 1980).

The removal of the terminal trityl hydroxyl blocking group may be achieved by conventional ways, conveniently first suspending the polynucleotide sequence in an acidic medium, conveniently about 75% to 85% acetic acid in water. After sufficient time for the reaction to occur, generally not exceeding about 2 hr, the DNA, RNA or combination thereof, may be precipitated by the addition of a small amount of a precipitant, e.g., ethanol or ether. The polynucleotide may then be isolated, conveniently by centrifugation, followed by at least partial neutralization by the addition of a small amount of a base, e.g., concentrated ammonium hydroxide, and the mixture evaporated to dryness.

For removal of an aroyl terminal blocking group concentrated aqueous ammonium hydroxide at elevated temperatures 40° to 70° C., for 2 to 6 h may be employed.

Occasionally, truncated sequences will occur from deprotection of the completed sequences with NH$_4$OH. As evidenced by several studies (see, e.g., *Organic Chemistry of Nucl. Acids, Part B* (eds. N. K. Kochetkov and E. I. Budovskii), Plenum Press, N.Y. (1972), p. 512.8; and Efcavitch, J. W. and Heiner, C. (1985) *Nucls, & Nuclt.* 4:267), this leads to two new classes of "failure" fragments: 5'-protected (e.g., 5'-DMT) and 5'-phosphoryl truncated sequences from the 5' and 3' halves of apurinic target DNA, respectively. The former class can pose problems in purification, since the 5'-protected truncated products are co-isolated with the 5'-protected target DNA.

In order to alleviate this problem, it is preferred in the present method that apurinic sites in the synthesized DNA strands be cleaved under conditions that do not hydrolyze the 3'-linkage of the DNA to the solid support, prior to enzymatic hydrolysis. This technique is based on the hydrolytic susceptibility of depurinated sites to mildly alkaline solutions of amines (see, e.g., Philippsen, P., et al., *BBRC* 33:922 (1968)). The synthesized polynucleotide chains are treated with the selected amine solution after deprotection and prior to enzymatic degradation as described above. The amine used in this step is one that will cause cleavage of a depurinated site; suitable amines may be either alkyl amines or aromatic amines and include, but are not limited to, lysine, ethylene diamine, aniline, cyclohexylamine, propylamine, and mixtures thereof. A particularly preferred amine solution is an aqueous lysine solution, pH 8-10. This additional purification step leads to a substantially cleaner product.

The resulting sequence can be used as a probe, can be used with DNA polymerase to form a double-stranded (ds) DNA or a plurality of fragments may be employed with partial complementarity so as to allow for overlapping, so as to produce a greatly extended sequence from the plurality of fragments. The fragments are annealed, so as to form a double strand having a plurality of nicks, and ligated.

Where a double-stranded sequence is obtained, the sequence may be manipulated in a variety of ways. The sequence may be directly inserted into a vector or virus, or may be modified by the addition of adaptors, linkers, or the like, where the resulting dsDNA may be inserted into a vector for cloning and subsequent restriction mapping or sequencing to ensure the presence of the desired sequence, or as appropriate, for expression.

Figure 1:
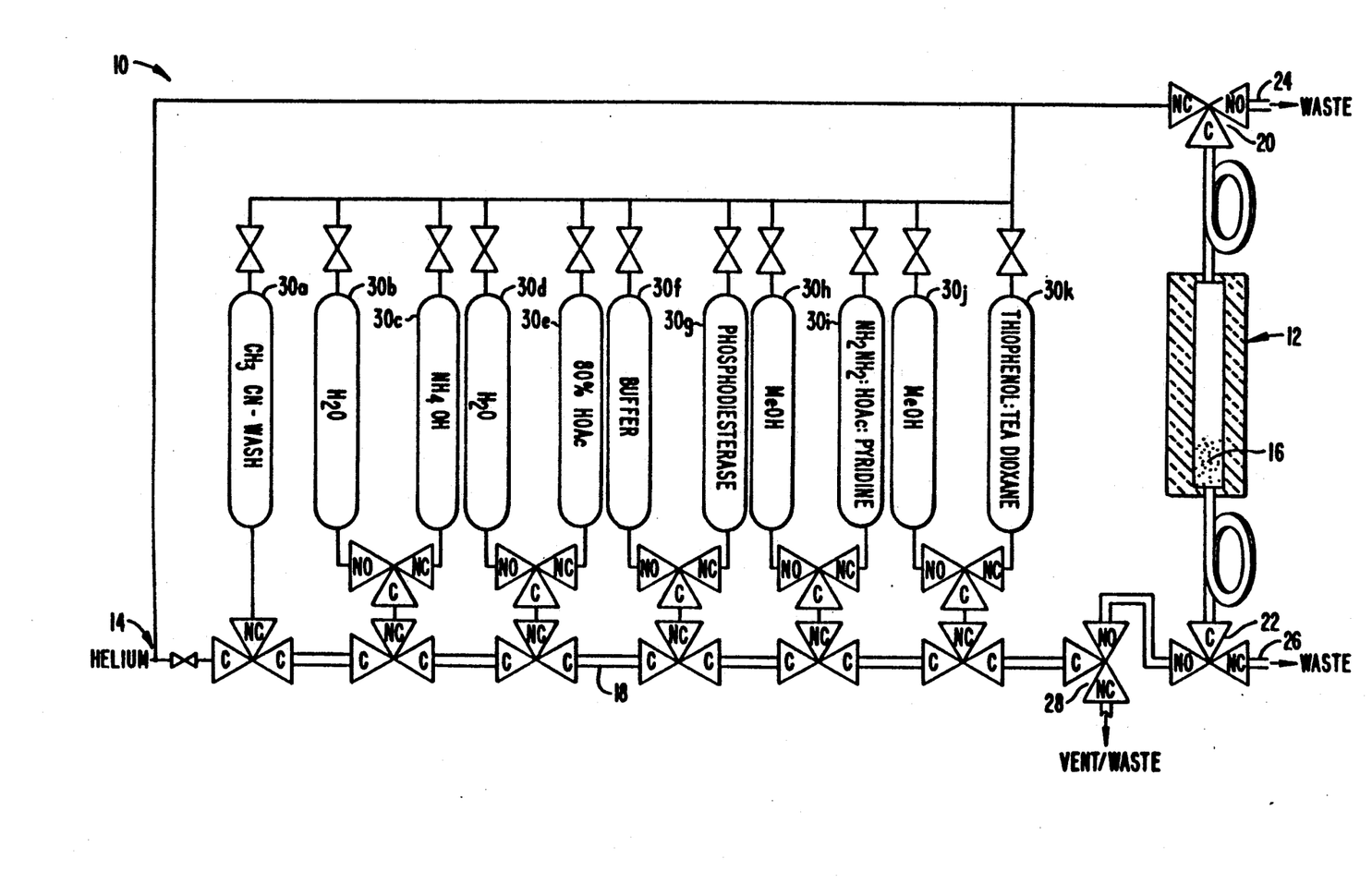
The Figure is a schematic diagram of an apparatus for use with the subject process for the preparation of oligonucleotides.

The preparation of the polynucleotides can be automated with a device as illustrated in the Figure. An automatic device for deblocking and purification 10 is provided having a temperature controlled reactor column 12 and a common helium source 14. The various valves are indicated as NC, normally closed; NO, normally open; and C, common valve or port.

The reactor column 12 is enclosed at either end by porous barriers. The pores in the barriers are sufficiently fine to retain the dispersed solid-phase support within the reactor while allowing for mixing without substantial pressure differentials. The packing 16 will be loosely packed. The reactor column 12 is separated from the reagent manifold 18 by an isolation valve 20 and from the helium manifold by isolation valve 22. Each of the valves 20 and 22 are connected to waste lines 24 and 26, respectively. The waste valve 28 is also a three-way, two-position automatic valve and has common and normally open ports connected to the reagent manifold 18.

The reagent manifold 18 connects a number of reagent and wash solution supply reservoirs: 30A, acetonitrile-wash; 30B, water; 30C, ammonium hydroxide; 30D, water; 30E, 80% acetic acid; 30F, buffer; 30G, phosphodiester base; 30H, methanol; 30I, hydrazine-acetic acid, pyridine; 30J, methanol; and 30K, thiophenoltriethylamine-dioxane.

Each of the reagent/wash solution pairs is connected to the reagent manifold 18 at a single entry point. It is preferred to make connection with a pair of valves in series. Wash or diluent solutions are coupled with reagent solutions, so they can be mixed and transferred to the reactor. Based on the previous description of various processes for preparing polynucleotides and the more detailed discussion in U.S. Pat. No. 4,483,964, as well as the procedure described in the Experimental section, it will be evident how the various valves may be operated to perform a deblocking and purification.

The following examples are offered by way of illustration and not by way of limitation.

EXPERIMENTAL

Example 1

Preparation of formamidine substituted guanosine

Into a reaction flask is introduced 6.7 g of deoxyguanosine, which is coevaporated with dimethylformamide (DMF). To the deoxyguanosine is added 8.75 ml of di-N-butylformamide dimethyl acetal (prepared as described by Meerwein et al, Liebigs Ann. (1961) 641:1) and 200 ml of DMF. The nucleoside dissolves rapidly but not completely within 3 hr. The clear yellowish solution is evaporated to an oil, partitioned in dichloromethane/aqueous sodium bicarbonate, the organic layer dried by evaporation, followed by dissolution in 100 ml of dichloromethane and then precipitated with 900 ml of petroleum ether. The supernatant is decanted, the precipitate redissolved in dichloromethane, and the dichloromethane evaporated to yield 12 g which is coevaporated with pyridine. To the mixture is then added 200 nl pyridine and 8.5 g of dimethoxytritylchloride and the reaction allowed to proceed at room temperature for 18 hr.

To the reaction mixture is added 10 ml methanol, the volatiles evaporated, and the residues partitioned between dichloromethane and aqueous sodium bicarbonate, followed by drying by evaporation and then coevaporation in toluene. To the resulting foam is added dichloromethane to dissolve the product and the product purified on silica. The ditritylated product is eluted with 1% methanol and dichloromethane, while the desired product is obtained with 2% to 3% methanol elution. The fractions containing the product are combined, concentrated by evaporation, and dissolved in 90 ml of dichloromethane, followed by precipitation with petroleum ether (900 ml) and isolated to yield 7.9 g of the desired product.

Example 2

Preparation of formamidine substituted adenosine

Prepared as described by Froehler and Matteucci, *Nucleic Acids Res.* (1983) 11:8031–8036.

Example 3

Preparation of levulinic acid capping agent

Levulinic acid (100 mmole) in diethyl ether (325 ml) and 50 mmole dicyclohexycarbodiimide were stirred for 60 hr. After filtration, the solvent was removed by distillation to yield 12 g of a yellowish oil. The oil was dissolved in 50 ml anhydrous tetrahydrofuran to provide a final concentration of 1M levulinic acid anhydride.

Example 4

Preparation of phosphoramidites

The trityl blocked nucleosides, with the exocyclic amines protected by the dibutylaminoformadinyl functionality or benzoyl functionality were carefully dried and reacted as follows. To 15 mmoles of the nucleoside is added 21 ml of diisopropylethylamine and 30 ml of chloroform and the mixture stirred under a nitrogen atmosphere. To the above mixture is then slowly added over about 1 min N,N-diisopropylaminomethoxyphosphorochloridite (4.3 ml). The addition is repeated and stirring continued for 20 min. To the mixture is then added 240 ml of ethyl acetate and the mixture transferred to a separatory funnel, flushed with nitrogen and 250 ml of degassed, saturated aq. NaCl solution added. Both phases are mixed with vigorous shaking, the phases allowed to separate, the aqueous phase removed and the extraction repeated three times. The organic phase is dried over sodium sulfate and then evaporated to dryness. To the residue is added 50 ml of toluene and the evaporation repeated. The residue is dissolved in 50 ml of toluene and the solution added dropwise to 600 ml of hexanes at $-70°$ C. with stirring under nitrogen. The phosphoramidite precipitates and is filtered and maintained in a desiccator under vacuum until used.

Example 5

Preparation of the solid support

Controlled pore glass (CPG) (25g, 500 Å pores) (ElectroNucleonics, MA) suspended in 95% ethanol (250 ml) was treated with 3-aminopropyltrimethoxysilane (7.5 ml) for 48 hr. After filtration and ethanol wash, the CPG was cured at 120° C. for 2 hr to give CPG-PrNH$_2$. Ten grams of this material was suspended in THF containing succinic anhydride (3.7 g) and 4-(N,N-dimethylamino)pyridine (0.5 g) added. The reaction was terminated after 48 hr, when the CPG no longer gave a positive test for amino function (ninhydrin in ethanol). Activation of the terminal carboxyl group was achieved with carbonyldiimidazole (4 g) in DMF for 18 hr in vacuo. The CPG was filtered and immediately suspended in DMF containing hexanediamine (4 g). After 48 hr, the CPG was filtered and washed extensively with methanol, dichloromethane, ether and then dried at 60° C. for 18 hr.

Example 6

Solid-supported DNA synthesis

Deprotection and enzymatic purification of slid-supported oligonucleotides.

The conjugation of the nucleoside to support was achieved by coupling of the deprotected deoxynucleoside 3'-O-succinic acid derivative to the functionalized amino terminal-CPG in accordance with the procedure of Chow et al., *Nucleic Acids Res.* (1981) 9:2807–2811.

The following is the cycle employed for the preparation of the polynucleotide, where the linking group between the CPG and the first nucleotide has the following formula:

The first nucleoside was thymidine which was 5'-dimethoxytrityl blocked. The monomer units were nucleosidyl substituted N,N-diisopropyl-O-methyl phosphoramidites. Adenosine and guanosine had the exocyclic nitrogen blocked with N,N-dibutylaminomethylene, so as to form an amidine with the exocyclic amine nitrogen, while cytosine had the exocyclic amine nitrogen blocked with benzoyl.

The following Table 1 indicates the cycle employed, employing 70 mg of the support, having approximately 3 μmole of thymidine.

TABLE 1*

| Cycle | | |
|---|---|---|
| 1 | Cleavage of DMT | 1 × 1 ml, 30 sec |
|   | 5% DCA in CH$_2$Cl$_2$ | 2 × 1 ml, flushthrough |
| 2 | Wash | |
|   | CH$_2$Cl$_2$ | 3 × 1 ml |
|   | CH$_3$CN (reagent) | 3 × 1 ml |
|   | CH$_3$CN (anh.) | 3 × 5 ml, Ar |
| 3 | Coupling | |
|   | 30 μmoles 5'-DMT-nucleoside phosphoramidite in anh. CH$_3$CN (0.5 ml) containing 250 μmoles 1H-tetrazole | 2 min |
| 4 | Wash | 0.5 ml |
|   | anh. CH$_2$CN | |
| 5 | Capping | |
|   | a. 0.5 M DMAP in THF/lutidine (9:1 v/v) | 0.5 ml |
|   | b 1M levulinic anh. in THF | 0.5 ml total 5 min |
| 6 * | Wash THF/2,6-lutidine/H$_2$O (8:1:1 v/v) | 1 ml, 15 sec |
| 7 | Oxidation 0.2M I$_2$ in THF/2,6-lutidine/H$_2$O (8:1:1 v/v) | 2 × 0.5 mL |
| 8 | Wash CH$_3$CN | 3 × 1 mL |
| 9 | Wash CH$_2$Cl$_2$ | 3 × 1 mL |

*DMT - p,p'-dimethoxytriphenylmethane
DCA - dichloroacetic acid
DMAP - 4-dimethylaminopyridine
lutidine - 2,6-dimethylpyridine
anh - anhydrous/anhydride
THF - tetrahydrofuran
v/v - volume/volume The cycle of 1 to 9 was repeated 14 times. After addition of the 14th nucleotide, the samples were split into 3 parts and the 3 cycles performed differently, by employing A, C, and G, respectively, for the 15th nucleotide and the 16th and 17th nucleotides were thymidine. A sample was taken before continuing the synthesis after the 15th nucleotide, where the oligonucleotides have as their last residue DMT-A, DMT-C, and DMT-G. These were used as controls for the enzymatic degradation, where with the final oligonucleotides, the compositions were split in half, one was completely deblocked and detritylated and the second was deblocked, but the DMT group was retained on the final thymidine. Both species were used in the enzyme reaction.

The following sequence was prepared:

3'-TTTTTTTTTTTTTTTXTT

X=A, C or G

The deprotection of the fragments, enzyme digestion and removal from the solid support was performed as follows. To the support was added 200 µl of dioxane/thiophenol/triethylamine (2:1:1) and the reaction performed at room temperature for 1 hr to ensure the complete removal of the methyl groups of the phosphate ester. The support was then thoroughly washed with methanol, followed by the addition of 200 µl 0.5M hydrazine·H$_2$O in pyridine/acetic acid (4:1 v/v) and the reaction carried out for 24 hr at room temperature, followed by methanol washing and then drying in high vacuum. This treatment removes all of the exocyclic amino protecting groups, as well as the levulinic capping group.

To 1-2 mg of the support from above suspended in 50 µl of 0.1M sodium acetate, pH 6.45, was added 3 units of spleen phosphodiesterase (Sigma P-0770) in 36 µl of glycerol/0.1M sodium succinate (1:1 v/v), pH 6.5 and the mixture maintained at 37° C. for 18 hr. At this time, the mixture was cooled, and the support thoroughly washed with 0.1M sodium acetate, pH 6.45 (100 µl).

To the washed support was added 200 µl of concentrated aq. ammonium hydroxide and the mixture allowed to stand for 2 hr at room temperature. The mixture was then centrifuged, and the supernatant isolated and evaporated to dryness in a Speed-vac.

The dry residue was resuspended in 100 µl 80% aqueous acetic acid and the reaction allowed to proceed at room temperature for one hour. The DNA was then precipitated by adding 1 ml ether, the dispersion centrifuged and the residue isolated. One drop of concentrated aq. ammonium hydroxide was added to the pellet and the pellet then evaporated to dryness in a Speed-vac. The container (Eppendorf tube) was washed down with 25 µl of distilled water and the pellet evaporated to dryness.

The products were analyzed by gel electrophoresis, where the samples were solubilized in 90% formamide/1% Ficoll/0.005% bromophenol blue (10 µl/mg support) and loaded onto a 20% polyacrylamide gel.

Based on the gel electrophoresis, where the preparation had been carried out in accordance with the subject invention, a sharp band was observed for the heptadecanucleotide, where there were only weakly observable intermediate bands, while the preparation where the blocking group was removed prior to enzyme treatment, showed the presence of a few bands of lower molecular weight, which were not as dark as the band obtained with the product prepared in accordance with the subject invention.

The following is an alternative protocol for the deprotection and purification protocol.
1. Detritylate the completed synthesis and wash with CH$_2$Cl$_2$.
2. Benzoylate 10 m with 2M benzoic anhydride in 6.5% N,N-dimethylaminopyridine (W/V) in 2,6-lutidine/THF (1:10 V/V), then wash with CH$_3$CN.
3. Demethylate phosphates for 1 h with thiophenol-triethylamine/dioxane (1:1:2 V/V) and wash with methanol.
4. Deprotect exocyclic nitrogen and 5'-O capping groups for 18 h with 0.5M hydrazine hydrate in pyridine/glacial acetic acid (4:1 V/V), then wash with methanol and 0.1M sodium phosphate, pH 6.0.
5. Digest for 18 h with 1 unit (per mg of support) of spleen phosphodiestetase in 0.1M sodium phosphate pH 6.0, then wash with 0.1M sodium phosphate, pH 6.0 and water.
6. Remove the fragment from the support with 2 H treatment with NH$_4$OH.
7. Transfer and seal supernatant in a glass vial for a 4 h debenzoylation at 60° C.
8. Dry in a Speed-Vac and resuspend in water.

Still another protocol makes use of an alkaline amine solution which, as described above, enables removal of 5'-DMT truncated fragments:
1. Detritylate the completed sequences and wash with CH$_2$Cl$_2$.
2. Benzoylate 10 m with 2M benzoic anhydride in 6.5% N,N-dimethylaminopyridine (w/v) in 2,6-lutidine/THF (1:10 v/v), then wash with CH$_3$CN.
3. Demethylate phosphates for 1 h with thiophenol/triethylamine/dioxane (1:1:2 v/v) and wash with methanol.
4. Deprotect exocyclic nitrogen and 5'-O capping groups for 18 h with 0.5M hydrazine hydrate in pyridine/glacial acetic acid (4:1 v/v), then wash with methanol and 0.1M sodium phosphate, pH 6.0.
5. Cleave apurinic sites with 1M lysine, pH 9, for 90 minutes, at 60° C., and wash with water.
6. Digest with 1 unit of (per mg support) alkaline phosphatase in 0.1M Tris, pH 8, for 2 hrs, at 37° C. and wash with 0.1M Tris, pH 8.
7. Digest with 1 unit (per mg of support) of spleen phosphodiesterase in 0.1M sodium phosphate, pH 6, and water.
8. Remove the fragment from the support with conc. NH$_4$OH for 1 hr at 20° C.
9. Transfer and seal supernatant in a glass vial and debenzoylate for 2 hrs at 60° C.
10. Dry in a Speed-Vac and resuspend in water.

Note: for beta-cyanoethyl phosphoramidites, it is preferred that a solution of t-butylamine in pyridine (1:9 v/v) be used as an alternative to the thiophenol/triethylamine/dioxane treatment of step 3.

Example 7

Preparation of phosphorylation reagent and 5'-phosphorylation of oligonucleotides The reagent bis($\beta$-cyanoethoxy)-N,N-diisopropylaminophosphine was synthesized as follows. Chloro-N,N-diisopropylamino-$\beta$-cyanoethoxyphosphine (N. D. Sinha, et al., *Nucl. Acid Res.* (1984) 12:4539; available from American Bionetics, Emeryville, Calif.) (4.6 mmoles) was added rapidly under argon to a stirred solution of 3-hydroxypropionitrile (4.6 mmoles) and N,N-diisopropylethylamine (DIPEA; 4.6 moles) in 10 ml methylene chloride at 0° C. The solution was allowed to warm to room temperature, diluted with ethyl acetate (50 ml) and washed with 80% saturated aqueous NaCl (2×20 ml). The organic phase was dried with anhydrous $Na_2SO_4$ and concentrated under reduced pressure. The oil was dissolved in ethyl acetate and then aliquoted into 1.5 ml septum-sealed vials each containing 200 μmole of the reagent. The solvent was removed by evacuation and the product was stored under argon at −20° C. This crude product was used without further purification. The reagent (2-cyanoethoxy)-2-(2'-4,4-dimethoxytrityloxyethylsulfonyl)ethoxy-N,N-diisopropylaminophosphine was synthesized as follows.

Commercially available sulfonyldiethanol (65% w/v in $H_2O$) was dried by repeated coevaporation with dry acetonitrile to give a viscous oil which crystallized on standing. To solid sulfonyldiethanol (10.6 g, 68.6 mmol) in pyridine (150 ml) was added 4,4'-dimethoxytrityl chloride (16.95 g, 50 mmole) and the mixture was left stirring in the dark for 18 h. The reaction solution was then concentrated in vacuo. The residue dissolved in ethyl acetate (500 ml) was extracted with 5% aq. $NaHCO_3$ and 80% saturated aq. NaCl and the organic phase was dried over anhydrous $Na_2SO_4$. After removal of solvents the product was purified by silica gel column chromatography to give 10.0 g of pure 2-4,4'-dimethoxytrityloxyethylsulfonylethanol:1 (TLC, silica in $CH_2Cl_2$; $R_f=0.015$). Chloro-N,N-diisopropylamino-2-cyanoethoxy-phosphine 2 (4.6 mmole) was added rapidly under argon to a stirred solution of 1 (4.6 mmole) and N,N-diisopropylethylamine (DIPEA; 4.6 mmole) in methylene chloride (10 ml) at 0° C. The solution was allowed to warm to room temperature, diluted with ethyl acetate (50 ml) and washed with 80% saturated aq. NaCl (2×20 ml). The organic phase was dried with anhydrous $Na_2SO_4$ and concentrated by rotary evaporation. The oily product was dissolved in acetonitrile and then aliquoted into 1.5 ml septum-sealed Wheaton vials each containing 100 μmole of phosphorylation reagent. The solvent was removed by evacuation and the product was stored under argon at −20° C. This crude product was used without further purification.

The dried materials were activated with tetrazole in acetonitrile and coupled to solid-supported oligonucleotides. Subsequently the synthetic DNA was oxidized with aqueous $I_2$ under standard conditions and deprotected with $NH_4OH$ at 60° C. This process gives the 5'-phosphorylated target fragment in quantitative yield. If the trityl containing phosphorylation reagent was used, the extent of coupling was determined from the absorption spectrum (498 nm) of an orange solution produced upon treatment of the oligomer with dichloroacetic acid in methylene chloride (5% w/v) prior to deprotection with $NH_4OH$.

Example 8

Solution Enzymatic purification of oligonucleotides in solution

The fragments 5'-TATCAATTCCAATAAACTT-TACTCCAAACC-3' and 5'-AAGGATCCAGTTG-GCAGTACAGCCTAGCAGCCATGGAAAC-3' were synthesized on the CPG support as described in Example 6 (Warner, et al., *DNA* 3, 401 (1984)). The fragments were then 5'-phosphorylated as described in Example 7. The oligomers were removed from the support with $NH_4OH$ at room temperature, then deprotected overnight at 60° C. The solution was evaporated to dryness in a speed-vac concentrator.

The crude product obtained from 2 mg of the support was suspended in 20 μl of $H_2O$ to which 50 μl of sodium phosphate buffer, pH 7.0 containing 0.3 units of spleen phosphodiestetase was added. After vortexing the solution was placed at 37° C. for 1 hour.

Polyacrylamide gel analysis revealed that truncated failure sequences were substantially degraded whereas the phosphorylated target fragment was protected from hydrolysis.

The subject invention has a number of advantages in providing for products free or substantially free of sequences which closely resemble the sequence of interest, but differ in significant ways in lacking one or more units. In accordance with the subject invention, oligomers or polymers are produced, where individual monomers are members of a group of monomers, rather than a single monomer and the oligomer or polymer is required to have a specific sequence of these monomers. In accordance with the subject invention, these oligomers or polymers may be produced free or substantially free of sequences, which are error sequences, which result from the failure of the addition of a particular monomer during the sequential formation of the oligomer. By employing the subject invention, the product obtained from the synthesis is in substantially pure form and may be used directly without contamination of closely analogous materials which may interfere with the use of the desired sequence, give erroneous results, and diminsh the efficiency with which the desired sequence may be employed. Furthermore, the method utilizes the extensive technology which presently exists for functionalizing a wide variety of functionalities with blocking and protecting groups, which blocking and protecting groups allow for sequential and/or simultaneous removal of such functionalities, while maintaining the oligomer or polymer bound to the support. Error sequences may then be destroyed by enzymatic hydrolysis, leaving only the desired sequences bound to the support. Any remaining blocking groups may then be removed in conjunction with cleavage from the support. In this manner, polynucleotides may be obtained which may be used directly as probes without the contamination of error sequences and polypeptides may be obtained which will not include a variety of other amino acid sequences which could interfere with an evaluation of the properties of the polypeptide, its use as an immunogen, or the like.

Although the foregoing invention has been described in some detail by way of illustration and example for purposes of clarity of understanding, it will be obvious that certain changes and modifications may be practiced within the scope of the appended claims.

What is claimed is:

1. In a method for preparing a polynucleotide containing a plurality of nucleotide monomers in a preselected order, in which (a) an individual terminal hydroxyl-blocked, O- and N-protected nucleotide monomer is added to available terminal hydroxyl groups on a fraction of a plurality of identical support-bound growing oligonucleotide chains, (b) terminal hydroxyl groups on the remaining fraction of growing oligonucleotide chains to which nucleotide monomer did not add and which chains thus constitute failure sequences, are capped with a capping group, (c) the terminal hydroxyl blocking group is selectively removed from the added terminal hydroxyl-blocked nucleotide monomer, steps (a), (b) and (c) are repeated serially until the last nucleotide in the preselected order has been added, and synthesis of the desired polynucleotide sequence is complete, and (d) thereafter the polynucleotide is cleaved from the support, the improvement which comprises:

employing as the terminal hydroxyl blocking group, a group which (a) is retained when removing the capping group and (b) prevents enzymatic hydrolysis of the completed polynucleotide;

employing as the capping group for capping the failure sequences, a group which is selectively removable while retaining the terminal hydroxyl blocking group;

after the last repetition of step (a), wherein the last terminal hydroxyl-blocked nucleotide monomer is added, removing the capping group, thereby forming decapped failure sequence oligonucleotides and terminal hydroxyl-blocked polynucleotide bound to the support;

contacting the decapped failure sequence oligonucleotides and terminal hydroxyl-blocked polynucleotide bound to the support with an enzyme capable of hydrolyzing the decapped failure sequence oligonucleotides under conditions effective to degrade the decapped failure sequence oligonucleotides and give rise to a support having substantially pure terminally blocked polynucleotide bound thereto; and removing the terminal blocking group and directly cleaving the polynucleotide in substantially pure form from the support.

2. A method according to claim 1, including the additional step of after the last nucleotide addition, but prior to removing any capping groups, substituting said terminal blocking group for an acid stable, base labile blocking group.

3. A method according to claim 2, wherein said acid stable, base labile group is a carboxylate.

4. A method according to claim 2, wherein said acid stable, base labile group is a phosphate.

5. A method according to claim 1, wherein prior to said enzymatic hydrolyzing, said oligonucleotide is treated with an aqueous amine solution having a pH of about 8 to 10.

6. A method according to claim 5, wherein said amine is selected from the group consisting of lysine, ethylene diamine, aniline, cyclohexylamine, propylamine, and mixtures thereof.

7. A method according to claim 6, wherein said amine is lysine.

8. A method according to claim 5, wherein prior to said enzymatic hydrolyzing, but after said amine treatment, said olignucleotide is treated with a phosphatase solution having a pH of about 8 to 10.

9. A method according to claim 1, wherein said nucleotide monomer is a phosphoramidite.

10. A method according to claim 1, wherein said nucleotide monomer is a phosphate ester.

11. A method according to claim 1, wherein said nucleotide monomer is O-protected with an alkyl or substituted alkyl group and N-protected with an aminomethylene moiety.

12. A method according to claim 11, wherein said capping group is levulinyl.

13. A method according to claim 12, wherein said terminal blocking group is trityl.

14. A method according to claim 12, wherein said aminomethylene moiety is removed with hydrazine.

15. A method according to claim 1, wherein said terminal blocking group is trityl.

16. A method according to claim 1, wherein when said nucleotide monomer is adenosine or guanosine, the monomer is N-protected with diisobutylaminomethylene.

17. A method according to claim 16, wherein when said nucleotide monomer is cytosine, the monomer is protected with a benzoyl or substituted benzoyl group.

18. In a method for preparing and purifying polypeptides employing terminal blocked amino acids, where the polypeptide is prepared by the sequential addition of terminally blocked O-, S- and N-protected amino acids, where the growing polypeptide is bound to a support through a selectively cleavable linkage, each sequential addition followed by removal of the terminal blocking group and the addition of the next amino acid, where after the final amino acid addition, the terminal blocking group and any protective groups are removed and the polypeptide cleaved from the support;

the improvement which comprises:

prior to each sequential addition, capping terminal groups which are not blocked with a capping group which may be selectively removed while retaining the terminal blocking group and linkage to the support;

after the last monomer addition, removing capping groups and any enzymatic hydrolysis interfering protective groups, while retaining the linkage to the support; and enzymatically hydrolyzing polypeptides lacking a terminal blocking group, prior to removal of the terminal blocking group and cleavage from the support.

19. A method according to claim 18, wherein said terminal blocking group is a N-oxycarbonyl group.

20. A method according to claim 19, wherein said capping group is a diacyl group capable of forming a cyclic imide.

21. In a method for preparing and purifying a polynucleotide, said method comprising the steps of:

sequentially adding to a growing nucleotide chain (1) joined to a support through a carboxylic acid ester linkage and (2) having a free terminal hydroxyl group, and O-blocked nucleosidyl phosphoramidite, to form a phosphite triester, oxidizing the phosphite triester to a phosphate ester and capping failed sequences by reacting free hydroxyl groups with an activated carboxylic acid to form a carboxylate ester, in a predetermined sequence;

removing O-blocking groups and repeating the above sequence, until addition of the terminal nucleosidyl phosphoramidite;

removal of phosphate ester protecting groups;

removal of amine protecting groups and capping groups; and removal of the polynucleotide chain from the support;

the improvement which comprises:

employing as nucleosidyl phosphoramidites, protected adenosine and guanosine, where the exocyclic amine is N,N-disubstituted aminomethylene substituted to form a formamidine, and protected cytosine, where the exocyclic amine is substituted with an aroyl group to form an amide;

capping with an oxo-substituted aliphatic carboxylic acid capable of forming a ring of from five to six annular members with hydrazine;

removal of the amine protecting groups and capping groups with hydrazine; and prior to removal of the terminal O-blocking group, digesting failure sequences with a phosphodiesterase.

22. A method according to claim 21, wherein said N,N-disubstituted aminomethylene is N,N-dialkyl.

23. A method according to claim 22, wherein said aroyl group is benzoyl.

24. A method according to claim 21, wherein said capping group is levulinate.

25. A method according to claim 21, wherein said hydrazine is employed in a pyridine solvent containing a pyridinium salt.

26. A method according to claim 21, including the steps of:

prior to removal of phosphate ester groups and after addition of the terminal nucleosidyl phosphoramidite, where the o-blocking group is a trityl group;

removing said trityl group under mildly acidic conditions; and reblocking by reaction of the unblocked hydroxyl with an aroyl anhydride in the presence of a tertiary amine or a phosphorylating agent.

27. A method according to claim 21, wherein said phosphorylating agent is a 0,0'-dicyanoethyl phosphoramidite, followed by oxidation to the phosphate.

28. A method according to claim 21, wherein said terminyl nucleosidyl phosphoramidite is a benzoate or phosphate blocked nucleosidyl phosphoramidite.

29. A method according to claim 21, wherein said phosphorylation agent is a 0-cyanoethyl-0'-(2'-0-4,4'-dimethoxytrityloxyethylsulfonyl)ethyl phosphoramidite, followed by oxidation.

* * * * *